United States Patent
Yi et al.

(10) Patent No.: US 12,046,367 B2
(45) Date of Patent: Jul. 23, 2024

(54) MEDICAL IMAGE READING ASSISTANT APPARATUS AND METHOD PROVIDING HANGING PROTOCOLS BASED ON MEDICAL USE ARTIFICIAL NEURAL NETWORK

(71) Applicant: Coreline Soft Co., Ltd., Seoul (KR)

(72) Inventors: Jaeyoun Yi, Seoul (KR); Donghoon Yu, Gimpo-si (KR); Hyeon Ji, Seoul (KR)

(73) Assignee: Coreline Soft Co., Ltd., Seoul (KR)

( * ) Notice: Subject to any disclaimer, the term of this patent is extended or adjusted under 35 U.S.C. 154(b) by 1049 days.

(21) Appl. No.: 16/896,801

(22) Filed: Jun. 9, 2020

(65) Prior Publication Data

US 2021/0035687 A1 Feb. 4, 2021

(30) Foreign Application Priority Data

Jul. 31, 2019 (KR) .................. 10-2019-0092909

(51) Int. Cl.
*G16H 50/00* (2018.01)
*A61B 6/00* (2006.01)
(Continued)

(52) U.S. Cl.
CPC .......... *G16H 50/20* (2018.01); *A61B 6/5217* (2013.01); *G06F 3/0481* (2013.01); *G06F 3/14* (2013.01); *G06T 7/0012* (2013.01); *G06V 10/82* (2022.01); *G16H 15/00* (2018.01); *G16H 30/40* (2018.01); *G16H 50/70* (2018.01); *A61B 5/055* (2013.01);
(Continued)

(58) Field of Classification Search
CPC ........ G16H 50/20; G16H 50/70; G16H 15/00; G16H 30/40; G06V 10/82; A61B 6/5217; A61B 5/055; A61B 6/032; G06F 3/0481; G06F 3/14; G06T 7/0012; G06T 2200/24; G06T 2207/10081; G06T 2207/10088;
(Continued)

(56) References Cited

U.S. PATENT DOCUMENTS 6,697,506 B1 * 2/2004 Qian .................. G06T 5/00
   382/128
8,165,368 B2   4/2012 Vijaykalyan et al.
(Continued)

FOREIGN PATENT DOCUMENTS

JP   2008-188214 A   8/2008
KR   10-1263705 B1   6/2013
(Continued)

*Primary Examiner* — Khai M Nguyen
(74) *Attorney, Agent, or Firm* — United One Law Group LLC; Kongsik Kim; Jhongwoo Peck

(57) ABSTRACT

Disclosed herein is a medical image reading assistant apparatus that provides hanging protocols based on a medical artificial neural network. The medical image reading assistant apparatus includes a computing system, and the computing system includes at least one processor. The at least one processor is configured to acquire or receive a first analysis result obtained through the inference of a first artificial neural network from a first medical image, to generate a first display setting based on the first analysis result, and to execute the first display setting so that the first medical image and the first analysis result are displayed on a screen based on the first display setting.

18 Claims, 8 Drawing Sheets

(51) Int. Cl.
  *G06F 3/0481* (2022.01)
  *G06F 3/14* (2006.01)
  *G06T 7/00* (2017.01)
  *G06V 10/82* (2022.01)
  *G16H 15/00* (2018.01)
  *G16H 30/40* (2018.01)
  *G16H 50/20* (2018.01)
  *G16H 50/70* (2018.01)
  *A61B 5/055* (2006.01)
  *A61B 6/03* (2006.01)

(52) U.S. Cl.
  CPC ........... *A61B 6/032* (2013.01); *G06T 2200/24* (2013.01); *G06T 2207/10081* (2013.01); *G06T 2207/10088* (2013.01); *G06T 2207/20081* (2013.01); *G06T 2207/20084* (2013.01); *G06T 2207/30004* (2013.01); *G06T 2207/30096* (2013.01)

(58) Field of Classification Search
  CPC . G06T 2207/20081; G06T 2207/20084; G06T 2207/30004; G06T 2207/30096
  See application file for complete search history.

(56) References Cited

U.S. PATENT DOCUMENTS

| | | | |
|---|---|---|---|
| 8,923,580 | B2 | 12/2014 | Dekel et al. |
| 9,152,760 | B2 | 10/2015 | Sherman et al. |
| 9,773,305 | B2 | 9/2017 | Lee et al. |
| 11,918,176 | B2* | 3/2024 | Oosake .............. A61B 1/00009 |
| 2005/0260770 | A1* | 11/2005 | Cohen ................ G01N 33/564 |
| | | | 436/518 |
| 2019/0130565 | A1* | 5/2019 | Lee ........................ G06N 3/08 |
| 2019/0371464 | A1 | 12/2019 | Kim et al. |
| 2022/0000351 | A1* | 1/2022 | Yamada ................. G16H 30/40 |
| 2023/0181160 | A1* | 6/2023 | Chiang ................. A61B 8/461 |
| | | | 600/444 |
| 2023/0210442 | A1* | 7/2023 | Krueger ................. A61B 3/14 |
| | | | 600/301 |

FOREIGN PATENT DOCUMENTS

| | | |
|---|---|---|
| KR | 10-2014-0091176 A | 7/2014 |
| KR | 10-2015-0006807 A | 1/2015 |
| KR | 10-1818074 B1 | 1/2018 |
| KR | 10-2018-0040287 A | 4/2018 |
| KR | 10-1923962 B1 | 11/2018 |
| KR | 10-1943011 B1 | 1/2019 |

* cited by examiner

MEDICAL IMAGE READING ASSISTANT APPARATUS AND METHOD PROVIDING HANGING PROTOCOLS BASED ON MEDICAL USE ARTIFICIAL NEURAL NETWORK

CROSS-REFERENCE TO RELATED APPLICATION

This application claims under 35 U.S.C. § 119(a) the benefit of Korean Patent Application No. 10-2019-0092909 filed on Jul. 31, 2019, which is incorporated herein by reference.

TECHNICAL FIELD

The present invention relates to an apparatus and method for supporting the reading of a medical image of a subject. More specifically, the present invention relates to a computing system for providing a hanging protocol, which is a setting in which a medical image is displayed, using an analysis result of a medical artificial neural network, and software that is executed in the computing system.

The present invention was derived from the research conducted as part of the Electronic System Industry Core Technology R&D Project sponsored by the Korean Ministry of Trade, Industry and Energy and the Korea Evaluation Institute of Industrial Technology [Task Serial Number: 1415160865; Detailed Task Number: 10072064; and Project Name: Development of Artificial Intelligence Source Technology for Supporting Reading of Lung, Liver and Heart Disease Images and Commercialization Associated with PACS].

BACKGROUND ART

Currently, medical images such as computed tomography (CT) images are widely used to analyze lesions and then use analysis results for diagnosis. For example, chest CT images are frequently used for reading because they enable readers to observe abnormalities in the body, such as the lungs, the bronchi, and the heart.

Some of the findings that can be read through chest CT images may be easily overlooked by human doctors because they are not easy to read and even radiologists can distinguish their features and forms only after years of training. In particular, when the difficulty of reading is high as in the reading of a lung nodule, the case of overlooking a lesion may occur even when a doctor pays a high degree of attention, which may lead to a trouble.

In order to assist in reading images that humans can easily overlook, the need for computer-aided diagnosis (CAD) has arisen. Conventional CAD technology is limited to assisting doctors in making decisions in a very limited area. For example, Korean Patent Application Publication No. 10-2014-0091176 and U.S. Pat. No. 9,773,305 disclose a conventional apparatus and method for assisting the diagnosis of lesions.

The reading of a lesion using CAD may include a process of identifying a suspected lesion first and then evaluating a score (e.g., confidence, malignancy, or the like) for that region. For example, if a plurality of nodules is found in the lungs, it will be necessary to specify a nodule that is expected to have the highest malignity and to determine future treatment plans.

Meanwhile, since there is a plurality of nodules, it is not known until reading which of the nodules is the most malignant. Accordingly, there frequently occurs a case where diagnosis is performed from a nodule whose actual malignity is not high or which is not expected to be highly malignant and thus the efficiency of reading is deteriorated. In addition, it is difficult to know which nodule is a real nodule before reading and reliability is low. Accordingly, when diagnosis is performed from a portion that is not expected to be an actual nodule, the efficiency of reading is also deteriorated.

Korean Patent No. 10-1943011 entitled "Method for Supporting Reading of Medical Image of Subject and Apparatus using the Same" proposes a method that introduces a score evaluation method into a conventional lesion detection system and allow a lesion with a higher score (e.g., confidence, malignancy, or the like) among detected lesions can be read first, thereby increasing the efficiency of reading, and also proposes an apparatus using the same.

Korean Patent No. 10-1943011 discloses technology in which when a number of lesions are detected for a single type of disease, a list in which entries are arranged from a lesion having the highest score, such as reliability, malignancy or the like, within a single display setting is displayed, and an image related to a selected lesion is displayed when a user selects the lesion from the list. Korean Patent No. 10-1943011 assumes a case where a plurality of types of lesions is detected for a single type of disease, and thus it does not propose a method corresponding to a case where lesions for a plurality of types of diseases are detected.

As to recent medical images such as computed tomography (CT) or magnetic resonance image (MRI) images, a medical image series is acquired through a single acquisition process, and the medical image series is not limited to a single type of lesion but may also be used to detect various types of lesions.

When a clinician or radiologist desires to identify various types of lesions on a single medical image series, it is necessary to improve the clinician or radiologist's workflows and hanging protocols. The hanging protocols refer to display settings for medical images.

There have been many prior arts intended to improve workflows and hanging protocols. For example, U.S. Pat. No. 8,165,368 entitled "Systems and Methods for Machine Learning Based Hanging Protocols" and U.S. Pat. No. 8,923,580 entitled "Smart PACS Workflow Systems and Methods Driven by Explicit Learning from Users" propose the technology that provides user-specific hanging protocols by learning a user's preference or a user's past display manipulation process.

Although the technologies of the prior art documents may optimize workflows and hanging protocols based on a user preference, a body part from which a medical image is acquired, and a past medical history, they do not propose workflows and hanging protocols based on diagnostic information or lesion information contained in a currently provided medical image.

SUMMARY OF THE DISCLOSURE

As to recent medical images such as CT or MRI images, a medical image series is acquired through a single acquisition process, and the medical image series is not limited to a single type of lesion but may also be used to detect various types of lesions. For example, for the lungs, a lung nodule as well as chronic obstructive pulmonary disease (COPD) may be diagnosed, emphysema may be diagnosed, and/or chronic bronchitis and/or an airway-related disease may also be diagnosed.

If a clinician or radiologist is provided with only a diagnostic list of lesions as in the prior art, the clinician or radiologist needs to select each lesion from the list and find and execute an appropriate display setting. In this case, a problem occurs in that the time required to execute or wait for a job that is not directly related to reading increases and thus the efficiency of a workflow is deteriorated.

If a clinician or radiologist can devote time only to tasks that are directly related to reading, it will shorten reading time and increase the efficiency of a workflow.

An object of the present invention is to provide hanging protocols that propose display layout settings appropriate for each type of lesion and disease based on image information and diagnostic information included in a medical image by considering a plurality of types of lesions that can be detected in the same body part and execute the display layout settings based on information related to the type of lesion and disease detected in the medical image.

An object of the present invention is to propose hanging protocols based on disease codes detected for medical images.

An object of the present invention is to execute hanging protocols based on disease codes detected in medical images in an environment having a CAD capable of detecting a plurality of types of lesions and to shorten reading time and increase the efficiency of a workflow so that a clinician or radiologist can devote time only to tasks that are directly related to reading.

An object of the present invention is to provide a user interface and display environment that increase the efficiency of reading, assist a clinician or radiologist in deriving a more accurate diagnosis result within a short period of time, and increase the accuracy of analysis.

According to an aspect of the present invention, there is provided a medical image reading assistant apparatus providing hanging protocols based on a medical artificial neural network, the medical image reading assistant apparatus including a computing system, the computing system including at least one processor. The at least one processor is configured to acquire or receive a first analysis result obtained through the inference of a first artificial neural network from a first medical image, to generate a first display setting based on the first analysis result, and to execute the first display setting by controlling a display device so that the first medical image and the first analysis result are displayed on a screen of the display device based on the first display setting.

The at least one processor may be further configured to execute the first display setting to include a user menu adapted to receive information about whether a user approves the first analysis result displayed on the screen based on the first display setting. The user menu may be provided in the form of a user interface that allows the user to select either "Confirm" or "Reject."

The at least one processor may be further configured to generate the first display setting based on at least one of the type of disease, the type of lesion, and a quantitative measurement result of the lesion detected in the first medical image and indicated by the first analysis result. The type of disease detected in the first medical image may be classified as a "disease code," and may be a basis for the generation of the first display setting.

The first display setting may include settings for at least one view of the first medical image related to the first analysis result, a menu adapted to display the first analysis result in the first medical image, the layout of the at least one view of the first medical image, and a user menu adapted to allow a user to respond to the first analysis result displayed in the first medical image. The first display setting may be referred to as a hanging protocol when specialized in the medical field.

The at least one processor may be further configured to, when the types of diseases detected in the first medical image and included in the first analysis result are plural in number, generate a plurality of sub-display settings for the plurality of types of diseases, respectively. In this case, the at least one processor may be further configured to arrange the plurality of sub-display settings in separate areas on the screen or to preferentially display a first sub-display setting among a plurality of sub-display settings on the screen. The at least one processor may be further configured to, when the first sub-display setting is preferentially displayed, display another sub-display setting instead of the first sub-display setting on the screen in response to user input.

The first artificial neural network may be an artificial neural network including the function of diagnosing a plurality of types of diseases for a single body part in a medical image.

The first artificial neural network may be implemented by combining a plurality of sub-artificial neural network modules including the function of diagnosing a single type of disease for a single body part in a medical image.

The first artificial neural network may be an artificial neural network that receives information obtained by at least an expert by diagnosing a plurality of types of diseases for a single body part included in a plurality of second medical images and learns the function of diagnosing the plurality of types of diseases included in the plurality of second medical images. In other words, in this case, the first artificial neural network may correspond to a case where an artificial neural network has learned the function of diagnosing a plurality of types of diseases via a single neural network model.

The computing system may further include a second artificial neural network that is an artificial neural network that receives a plurality of second display settings selected by at least an expert for a plurality of types of diseases diagnosed for a plurality of third medical images and learns the function of generating display settings based on the types of diseases diagnosed. In this case, the at least one processor may be further configured to input the first analysis result to the second artificial neural network and to control the second artificial neural network so that the first display setting is acquired through the inference of the second artificial neural network.

The computing system may further include a third artificial neural network that is an artificial neural network that receives a plurality of third display settings selected by at least an expert for a plurality of third analysis results obtained through the inference of the first artificial neural network for a plurality of third medical images and learns correlations between at least one of the type of disease, the type of lesion, and a quantitative measurement result of the lesion, detected in the plurality of third medical images and included in the plurality of third analysis results, and the plurality of third display settings. In this case, the at least one processor may be further configured to input the first analysis result to the third artificial neural network and to control the third artificial neural network so that the first display setting is acquired through the inference of the third artificial neural network.

According to another aspect of the present invention, there is provided an artificial neural network-based medical image reading assistant method, the artificial neural network-based medical image reading assistant method being performed by program instructions executed by a computing system, the computing system including at least one processor, the artificial neural network-based medical image reading assistant method including: acquiring or receiving, by the at least one processor, a first analysis result obtained through the inference of a first artificial neural network from a first medical image; generating, by the at least one processor, a first display setting based on the first analysis result; and executing, by the at least one processor, the first display setting by controlling a display device so that the first medical image and the first analysis result are displayed on a screen of the display device based on the first display setting.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE DISCLOSURE

Other objects and features of the present invention in addition to the above object will be apparent from the following description of embodiments with reference to the accompanying drawings.

Embodiments of the present invention will be described in detail below with reference to the accompanying drawings. In the following description, when it is determined that a detailed description of a related known component or function may unnecessarily make the gist of the present invention obscure, it will be omitted.

Deep learning/CNN-based artificial neural network technology, which has recently developed rapidly, is considered for the purpose of identifying a visual element that is difficult to identify with the human eye when it is applied to the imaging field. The field of application of the above technology is expected to expand to various fields such as security, medical imaging, and non-destructive testing.

For example, in the medical imaging field, there are cases where a tissue in question is not immediately diagnosed as a cancer tissue in a biopsy state but whether it is a cancer tissue is determined only after being monitored from a pathological point of view. Although it is difficult to confirm whether a corresponding cell is a cancer tissue in a medical image with the human eye, there is an expectation that the application of artificial neural network technology may acquire more accurate prediction results than observation with the human eye.

It is expected that this artificial neural network technology is applied and performs the analysis process of detecting a disease or lesion difficult to identify with the human eye in a medical image, segmenting a region of interest such as a specific tissue, and measuring the segmented region.

The present invention relates to a medical image reading support system that provides a configuration that visualizes various analysis techniques, to which such artificial neural network technology is applied, in the most appropriate form that can be read by human experts.

Figure 1:
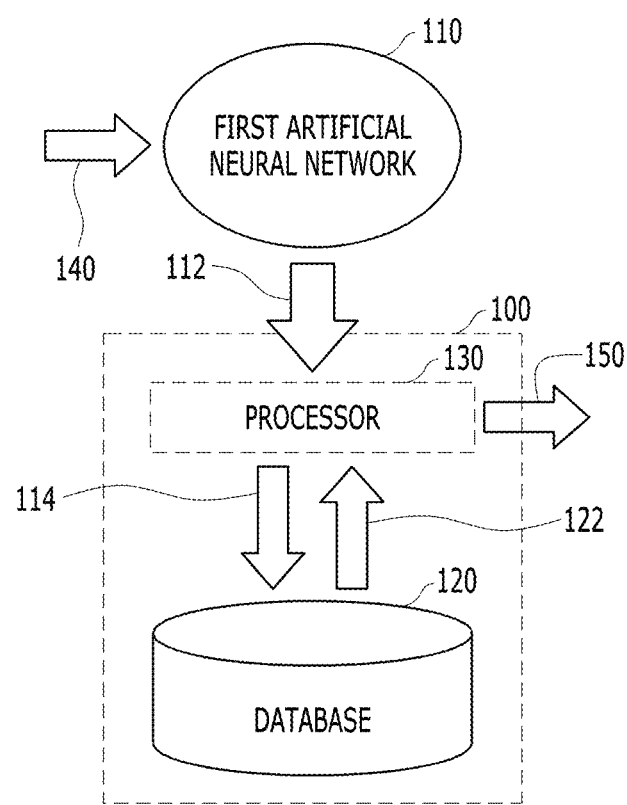
FIG. 1 is a diagram showing a medical image reading assistant apparatus providing hanging protocols based on a medical artificial neural network according to an embodiment of the present invention.

FIG. 1 is a diagram showing a medical image reading assistant apparatus providing hanging protocols based on a medical artificial neural network according to an embodiment of the present invention.

Referring to FIG. 1, the medical image reading assistant apparatus providing hanging protocols based on a medical artificial neural network according to the present embodiment includes a computing system 100, and the computing system 100 includes at least one processor 130. The computing system 100 may further include a database 120. The at least one processor 130 acquires or receives a first analysis result 112 obtained through the inference of a first artificial neural network 110 from a first medical image 140, generates a first display setting 150 based on the first analysis result 112, and executes the first display setting 150 so that the first medical image 140 and the first analysis result 112 are displayed on a screen based on the first display setting 150.

The at least one processor 130 may execute the first display setting 150 to include a user menu adapted to receive information about whether a user approves the first analysis result 112 displayed on the screen based on the first display setting 150. The user menu may be provided in the form of a user interface that allows the user to select either "Confirm" or "Reject."

The at least one processor 130 may generate the first display setting 150 based on at least one of the type of disease, the type of lesion, and a quantitative measurement result of the lesion detected in the first medical image 140 and indicated by the first analysis result 112. The type of disease detected in the first medical image 140 may be classified as a "disease code," and may be a basis for the generation of the first display setting 150.

The first display setting 150 may include settings for at least one view of the first medical image 140 related to the first analysis result 112, a menu adapted to display the first analysis result 112 in the first medical image 140, the layout of the at least one view of the first medical image 140, and a user menu adapted to allow a user to respond to the first analysis result 112 displayed in the first medical image 140.

More specifically, the first display setting 150 may include settings for a plurality of views of the first medical image 140 related to the first analysis result 112, a visualized menu adapted to display the first analysis result 112 in at least one of the plurality of views of the first medical image 140, a visualized menu adapted to display a related portion in the first medical image 140 clinically related to the first analysis result 112, the layout of the plurality of views of the first medical image 140, a visual/audible expression adapted such that the first analysis result 112 and the related portion in the first medical image 140 clinically related to the first analysis result 112 are synchronized among the plurality of views of the first medical image 140, and a user menu configured to allow a user to respond to the first analysis result 112 displayed in at least one of the plurality of views of the first medical image 140 and/or the related portion clinically related to the first analysis result 112 displayed in the first medical image 140. The first display setting 150 is referred to as a hanging protocol when specialized in the medical field.

For general information regarding the hanging protocols, reference may be made to the above-described U.S. Pat. No. 8,165,368 entitled "Systems and Methods for Machine Learning Based Hanging Protocols" and U.S. Pat. No. 8,923,580 entitled "Smart PACS Workflow Systems and Methods Driven by Explicit Learning from Users."

The processor 130 may generate the first display setting 150 based on rules adapted to generate hanging protocols, which are stored in the database 120. In other words, the processor 130 may extract the first analysis result 112 or the principal features of the first analysis result 112, and may sends a query 114 to the database 120. The database 120 may provide the processor 130 with a hanging protocol response 122 related to the query 114 based on the rules stored in the database 120 in response to the query 114. When the first analysis result 112 includes a plurality of disease codes, the processor 130 may generate a query 114 for each of the disease codes, may transmit it to the database 120, and may generate the first response settings 150 by combining hanging protocol responses 122 received from the database 120 or by assigning priorities to the hanging protocol responses 122. The processor 130 may transmit the first display setting 150 to a display device, and may control the display device so that the first display setting 150 is executed on the screen of the display device.

Furthermore, when the first analysis result 112 is a provisional or preliminary reading result, a plurality of disease codes is detected in the first analysis result 112 and the likelihood of being a lesion or disease for at least one disease code is detected as being a critical likelihood or higher, the processor 130 may generate the first display setting 150 according to a rule-based hanging protocol corresponding to the lesion or disease detected as having the critical likelihood or higher.

Rules indicative of correlations between provisional or preliminary reading results and hanging protocol layouts may be stored in the database 120. Furthermore, when a provisional or preliminary reading result includes a plurality of disease codes, rules adapted to designate hanging protocol layouts related to the respective disease codes may be stored in the database 120.

Furthermore, when the first analysis result 112 includes the diagnosis of a disease or lesion, the segmentation of a specific region of interest, and the measurement result of a segmented region, the processor 130 may transmit a query 114 to the database 120 based on the type of each result, may receive hanging protocol responses 122 to respective queries 114, and may generate the first display setting 150 by combining or coupling the hanging protocol responses 122 for the respective queries 114 or by assigning priorities to and arranging the hanging protocol responses 122. In this case, rules adapted to define corresponding hanging protocol settings based on the types of results that the first analysis result 112 may include may be stored in the database 120.

The first artificial neural network 110 may be an artificial neural network including a function capable of diagnosing a plurality of types of diseases for a single body part in a medical image.

The first artificial neural network 110 may be implemented by combining a plurality of sub-artificial neural network modules including the function of diagnosing a single type of disease for a single body part in a medical image.

The first artificial neural network 110 may be an artificial neural network that receives information obtained by at least an expert by diagnosing a plurality of types of diseases for a single body part included in a plurality of second medical images and diagnosing the plurality of types of diseases included in the plurality of second medical images. In other words, in this case, the first artificial neural network 110 may correspond to a case where an artificial neural network has learned the function of diagnosing a plurality of types of diseases via a single neural network model.

When the types of diseases detected in the first medical image 140 and included in the first analysis result 112 are plural in number, the at least one processor 130 may generate a plurality of sub-display settings for the plurality of types of diseases, respectively. In this case, the at least one processor 130 may arrange the plurality of sub-display settings in separate areas on the screen.

Alternatively, according to another embodiment of the present invention, the at least one processor 130 may preferentially display a first sub-display setting among a plurality of sub-display settings on a screen. When the first sub-display setting is preferentially displayed, the at least one processor 130 may display another sub-display setting instead of the first sub-display setting on the screen in response to user input (which may be designated as a specific function key promised in advance, e.g., a "Tab" key).

A factor determining the first display setting 150 provided by the processor 130 is information included in the first medical image 140, and is information included in the first analysis result 112 obtained by the analysis and inference of the first artificial neural network 110. The first display setting 150 based on the first analysis result 112 may be derived through the association between clinical features (disease codes) or functional features (segmentation, detection, identification, diagnosis, or measurement) included in the first analysis result 112 and the rules stored in database 120.

Figure 2:
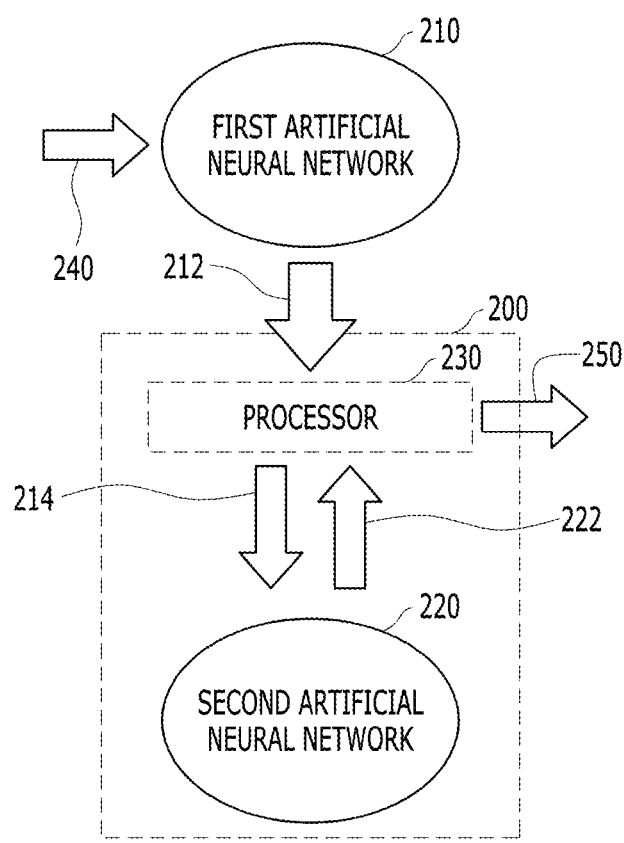
FIG. 2 is a diagram showing a medical image reading assistant apparatus providing hanging protocols based on a medical artificial neural network according to an embodiment of the present invention.

FIG. 2 is a diagram showing a medical image reading assistant apparatus providing hanging protocols based on a medical artificial neural network according to an embodiment of the present invention.

Since the first artificial neural network 210, first medical image 240, and first analysis result 212 of FIG. 2 are the same as the first artificial neural network 110, first medical image 140, and first analysis result 112 of FIG. 1, redundant descriptions will be omitted.

The computing system 200 may further include a second artificial neural network 220 that is an artificial neural network that receives a plurality of second display settings selected by an expert for a plurality of types of diseases diagnosed for a plurality of third medical images and learns the function of generating display settings based on the types of diseases diagnosed. In other words, disease codes may be provided as input during the learning of the second artificial neural network 220, and the second artificial neural network 220 may be trained to predict a plurality of second display settings selected by an expert for the disease codes. In this case, the at least one processor 230 may input the first analysis result 112 to the second artificial neural network 220 (see an input 214), and may control the second artificial neural network 220 so that the first display setting 250 is acquired through the inference 222 of the second artificial neural network 220.

Alternatively, according to another embodiment of the present invention, the computing system 200 may further include a third artificial neural network (not shown) that is an artificial neural network that receives a plurality of third display settings selected by an expert for a plurality of third analysis results obtained through the inference of the first artificial neural network 210 for a plurality of third medical images and learns correlations between at least one of the type of disease, the type of lesion, and a quantitative measurement result of the lesion, detected in the plurality of third medical images and included in the plurality of third analysis results, and the plurality of third display settings. In this case, the at least one processor 230 may input the first analysis result 212 to the third artificial neural network, and may control the third artificial neural network so that the first display setting 250 is acquired through the inference of the third artificial neural network.

Figure 3:
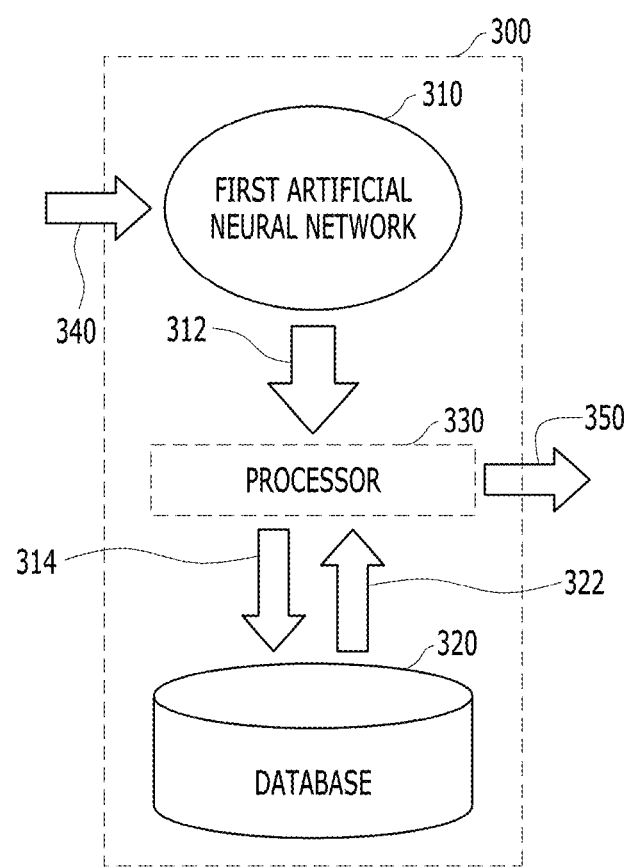
FIG. 3 is a diagram showing a medical image reading assistant apparatus providing hanging protocols based on a medical artificial neural network according to an embodiment of the present invention.

FIG. 3 is a diagram showing a medical image reading assistant apparatus providing hanging protocols based on a medical artificial neural network according to an embodiment of the present invention.

Referring to FIG. 3, the medical image reading assistant apparatus providing hanging protocols based on a medical artificial neural network according to the present embodiment includes a computing system 300, and the computing system 300 includes at least one processor 330. The computing system 300 may further include a first artificial neural network 310 and a database 320. The at least one processor 330 acquires or receives a first analysis result 312 obtained through the inference of the first artificial neural network 310 for a first medical image 340, generates a first display setting 350 based on the first analysis result 312, and executes the first display setting 350 so that the first medical image 340 and the first analysis result 312 are displayed on a screen based on the first display setting 350.

The at least one processor 330 may execute the first display setting 350 to include a user menu adapted to receive information about whether a user approves the first analysis result 312 displayed on the screen based on the first display setting 350. The user menu may be provided in the form of a user interface that allows the user to select either "Confirm" or "Reject."

The at least one processor 330 may generate the first display setting 350 based on at least one of the type of disease, the type of lesion, and a quantitative measurement result of the lesion detected in the first medical image 340 and indicated by the first analysis result 312. The type of disease detected in the first medical image 340 may be classified as a "disease code," and may be a basis for the generation of the first display setting 350.

The first display setting 350 may include settings for at least one view of the first medical image 340 related to the first analysis result 312, a menu adapted to display the first analysis result 312 in the first medical image 340, the layout of the at least one view of the first medical image 340, and a user menu adapted to allow a user to respond to the first analysis result 312 displayed in the first medical image 340. The first display setting 350 may be a hanging protocol that is specialized in the medical field.

Figure 4:
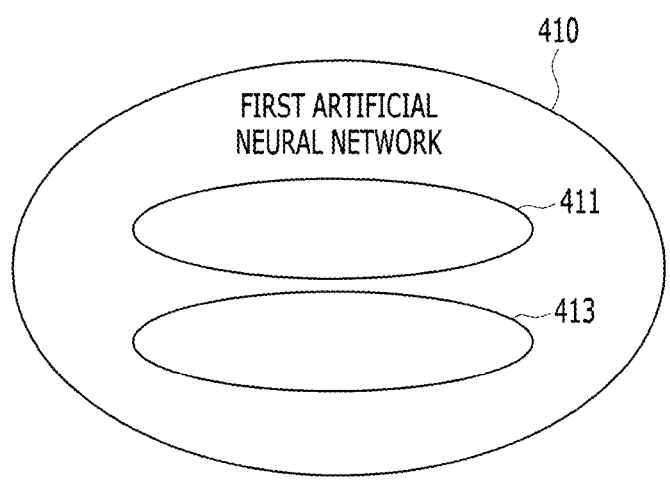
FIG. 4 is a diagram showing an example of a first artificial neural network of a medical image reading assistant apparatus providing hanging protocols based on a medical artificial neural network according to an embodiment of the present invention.

FIG. 4 is a diagram showing an example of a first artificial neural network 410 of a medical image reading assistant apparatus providing hanging protocols based on a medical artificial neural network according to an embodiment of the present invention.

The first artificial neural network 410 may be an artificial neural network including the function of diagnosing a plurality of types of diseases for a single body part in a medical image.

The first artificial neural network 410 may be implemented by combining a plurality of sub-artificial neural network modules 411 and 413 including the function of diagnosing a single type of disease for a single body part in a medical image. For example, the first sub-artificial neural network module 411 may be an artificial neural network module trained to detect a lung nodule, and the second sub-artificial neural network module 413 may be an artificial neural network module trained to diagnose emphysema.

The first artificial neural network 410 is not limited to the embodiment of FIG. 4. In an artificial neural network based medical image reading assistant apparatus according to another embodiment the present invention, a first artificial neural network may be an artificial neural network that receives information obtained by an expert by diagnosing a plurality of types of diseases for a single body part included in a plurality of second medical images and learns the function of diagnosing the plurality of types of diseases included in the plurality of second medical images. In other words, in this case, the first artificial neural network may correspond to a case where an artificial neural network has learned the function of diagnosing a plurality of types of diseases via a single neural network model. In this case, in a process of the learning of the first artificial neural network, a plurality of second medical images may be provided as input, and a plurality of types of diseases may be provided as metadata. Furthermore, whether each medical image corresponds to a disease may be provided as a variable to be predicted by the first artificial neural network. Unlike a common artificial neural network that diagnoses a single disease, the first artificial neural network may be trained to diagnose a plurality of types of diseases for a single body part from the beginning by adding a plurality of types of diseases and whether images correspond to the diseases as metadata.

Figure 5:
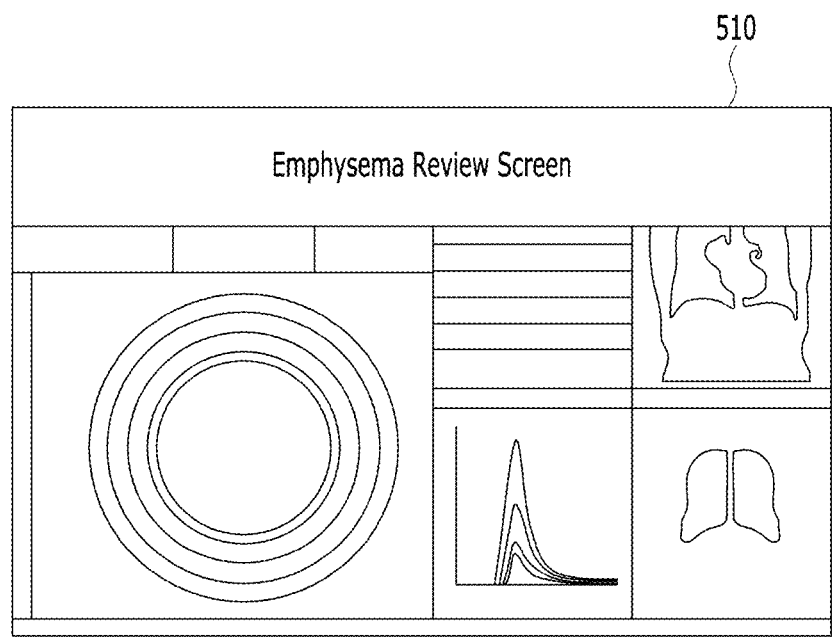
FIG. 5 is a diagram showing an example in which a first display setting based on a first analysis result of a first artificial neural network according to an embodiment of the present invention is executed.

FIG. 5 is a diagram showing an example in which a first display setting based on a first analysis result of a first artificial neural network according to an embodiment of the present invention is executed.

When according to the first analysis result of the first artificial neural network, the first medical image indicates that the likelihood of being diagnosed as emphysema is a critical likelihood or higher, the processor may generate and execute a preset display setting 510 in order to read emphysema. Emphysema and/or chronic bronchitis are known to be the cause of Chronic Obstructive Pulmonary Disease (COPD). COPD is also highly related to emphysema and chronic bronchitis, and COPD patients often have both emphysema and chronic bronchitis. Emphysema is a disease in which the lungs lose elasticity due to the destruction of the walls of the alveoli attributable to harmful substances such as cigarettes and the access of air is not free. It may be advantageous for a clinician or radiologist making a clinical decision about emphysema to display a CT image together with measurement results or statistical analysis rather than simply displaying a CT image.

Alternatively, according to another embodiment of the present invention, when a plurality of disease codes appear in a first medical image, at least one processor selects a specific disease code as a first disease code, and may preferentially display a first sub-display setting corresponding to the first disease code on a screen. In other words, the plurality of disease codes are related to a plurality of sub-display settings, respectively, and the processor may preferentially display the first sub-display setting corresponding to the first disease code among the plurality of sub-display settings. When the first sub-display setting is preferentially displayed, the at least one processor may display another sub-display setting instead of the first sub-display setting on the screen in response to user input (e.g., the pressing of a specific function key).

Figure 6:
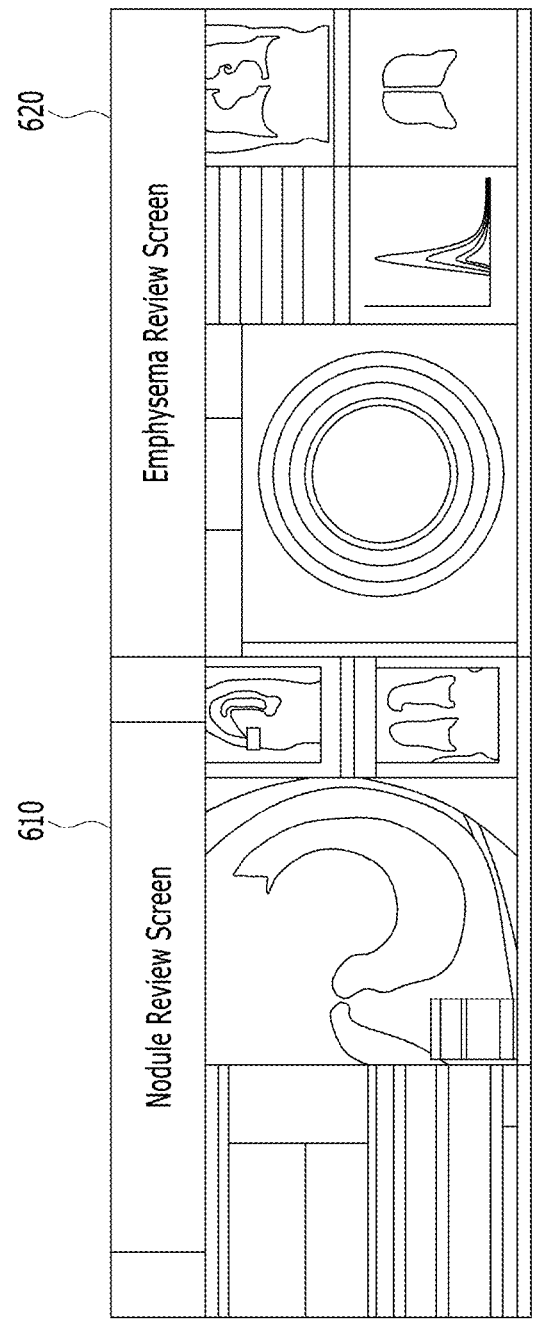
FIG. 6 is a diagram showing an example in which a first display setting based on a first analysis result of a first artificial neural network according to an embodiment of the present invention is executed.

FIG. 6 is a diagram showing an example in which a first display setting based on a first analysis result of a first artificial neural network according to an embodiment of the present invention is executed.

When the types of diseases detected in the first medical image and included in the first analysis result are plural in number, the at least one processor may generate a plurality of sub-display settings for the plurality of types of diseases, respectively. In this case, the at least one processor may arrange the plurality of sub-display settings in separate areas on the screen.

Referring to FIG. 6, there is shown a case in which two disease codes are derived from the first analysis result. A first sub-display setting 610 may include efficient screen layout and an efficient user interface in order to detect and diagnose a pulmonary nodule, and a second sub-display setting 620 may include effective screen layout, the efficient configurations of screen modules and an efficient user interface in order to diagnose emphysema.

Even in the case of the same image, the same body part and the medical image of the same organ, when a different lesion is diagnosed, the configuration and layout of a screen may be changed accordingly. The layout of a screen, the type of image disposed on the screen, the view of the image disposed on the screen, a user menu disposed on the screen, and the function of the user menu may be changed.

Furthermore, rules may be defined to determine a lesion/disease having a higher priority among various types of lesions/diseases by referring to the gender, age and past medical history of a subject and to start from a hanging protocol for the determined lesion/disease.

Alternatively, hanging protocols/display settings may be defined to display a display setting for a lesion/disease having a first priority so that the display setting is most prominently visualized on the screen (e.g., the display setting is placed in the largest area or is most visually emphasized) and to remarkably display a display setting having a subsequent priority after a clinician or radiologist has read the lesion/disease having a first priority based on the display setting having a first priority.

When a plurality of disease codes is included in the first analysis result, the priorities of disease codes may be determined in advance. The priorities may be determined in advance according to the severity of their disease. Alternatively, the priorities may be adaptively determined according to the severity of their disease appearing in the first analysis result.

In a medical image reading assistant apparatus according to an embodiment of the present invention, when a lesion or disease corresponding to a specific disease code is detected in the first analysis result generated by the first artificial neural network, a user display setting on a screen corresponding to the specific disease code may be optimized. The disease code may be classified by the first artificial neural network.

Figure 7:
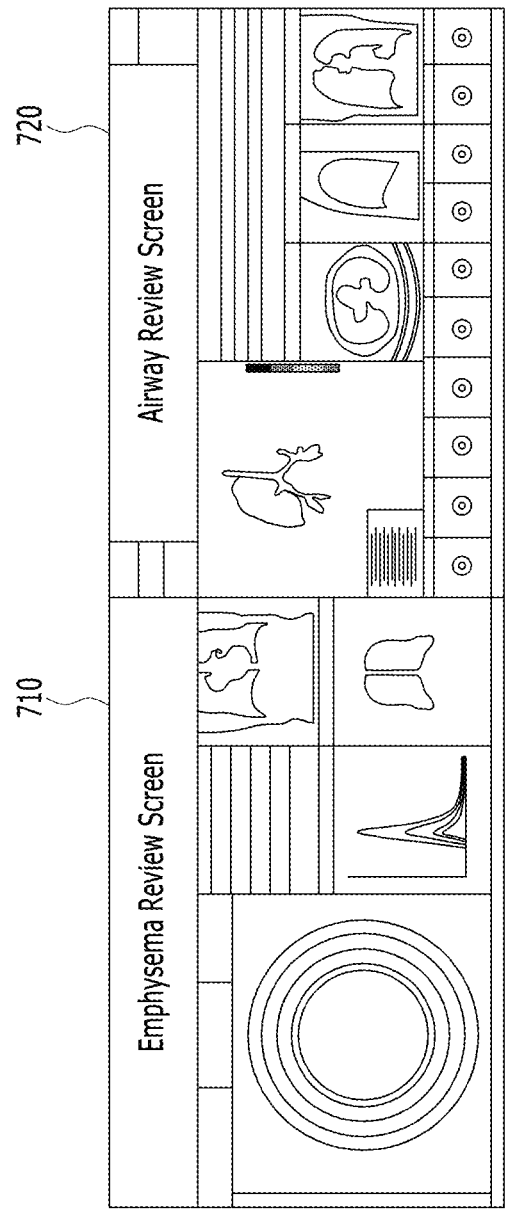
FIG. 7 is a diagram showing an example in which a first display setting based on a first analysis result of a first artificial neural network according to an embodiment of the present invention is executed.

FIG. 7 is a diagram showing an example in which a first display setting based on a first analysis result of a first artificial neural network according to an embodiment of the present invention is executed.

When a plurality of analysis results affecting a plurality of disease or a single disease requires the review of a clinician or radiologist, the plurality of analysis results are allocated to and displayed in separate area on the screen.

FIG. 7 shows a case in which emphysema and airway thickness are selected as candidate diseases having a high likelihood of disease, respectively.

In FIG. 7, the first sub-display setting 710 is an example of a display setting appropriate for emphysema. The second sub-display setting 720 is an example of a display setting appropriate for checking the thickness of the airway. The second sub-display setting 720 includes the result of the segmentation of the airway and a quantitative measurement based on the segmentation of the airway, and the first sub-display setting 710 and the second sub-display setting 720 may be displayed in separate areas on the screen.

An artificial neural network-based medical image reading assistant apparatus according to an embodiment of the present invention includes a computing system, and the computing system includes at least one processor. When the computing system acquires a first medical image such as a CT image or receives an already acquired first medical image, a first artificial neural network generates a first analysis result including an automatic analysis result through inference from the first medical image. The provisional or preliminary reading of the first medical image is performed by the analysis of the first artificial neural network, and the processor provides a displayed screen to a medical staff (who may include all of a clinician, a radiologist, and a technical staff) according to a hanging protocol based on the result of the provisional or preliminary reading. The medical staff may check on the screen a lesion, a disease, or a quantitative measurement result to be checked according to the result of the provisional or preliminary reading. Visualization elements are arranged on the screen so that the medical staff can easily view the lesion, the disease, or the quantitative measurement result on the screen and make a clinical decision, and the first medical image may be provided as various views through an image processing process as needed.

The medical staff may view the displayed screen, may make a clinical decision, and may then enter "Confirm/Reject" for the lesion, disease, or quantitative measurement result displayed on the screen. "Confirm/Reject" may be received by the user menu provided to the medical staff through the user interface, and the clinical decision is incorporated into "Confirm/Reject."

A factor determining the hanging protocol is information included in the first medical image, and is information included in the first analysis result generated by the analysis of the first artificial neural network.

Figure 8:
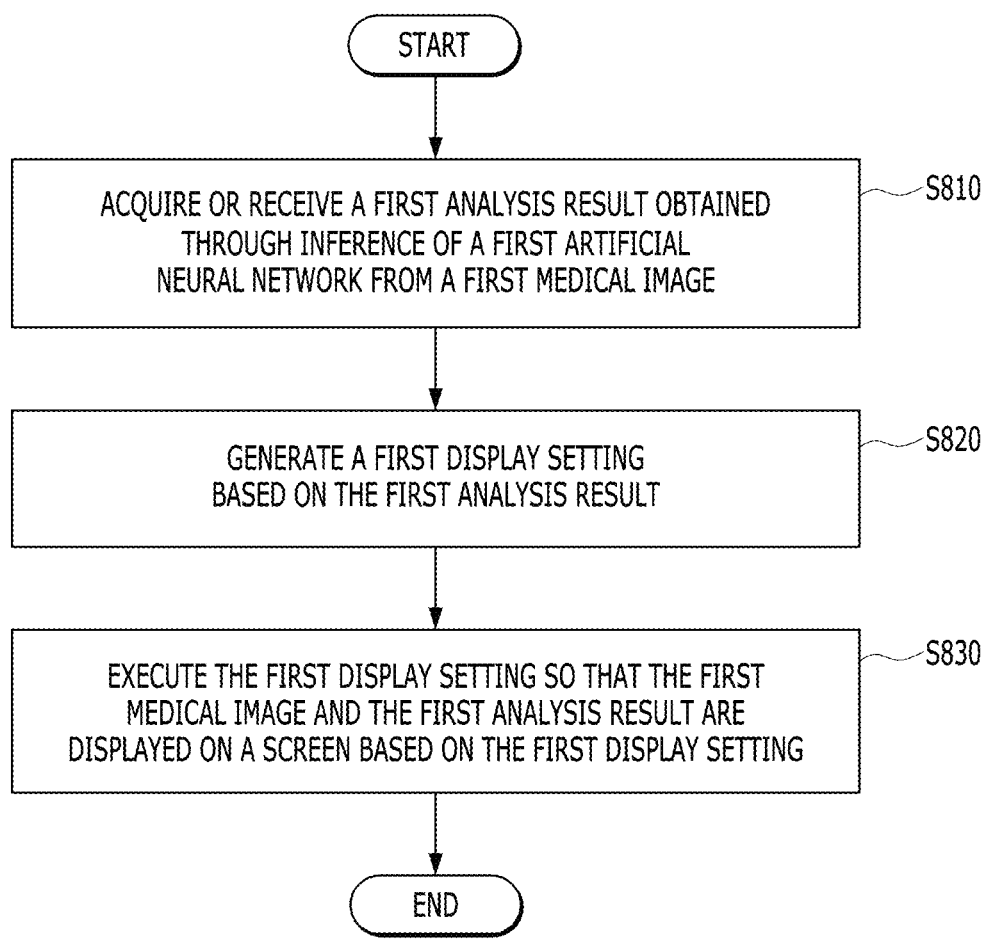
FIG. 8 is an operation flowchart showing an artificial neural network-based medical image reading assistant method according to an embodiment of the present invention.

FIG. 8 is an operation flowchart showing an artificial neural network-based medical image reading assistant method according to an embodiment of the present invention.

Referring to FIGS. 8 and FIGS. 1 to 3 together, the artificial neural network-based medical image reading assistant method according to the present embodiment is performed by the computing system 100, 200 or 300, the computing system 100, 200 or 300 includes the at least one processor 130, 230 or 330. The method according to the present invention includes: step S810 of acquiring or receiving, by the at least one processor 130, 230, 330, the first analysis result 112, 212 or 312 obtained through the inference of the first artificial neural network 110, 210 or 310 for the first medical image 140, 240 or 340; step S820 of generating, by the at least one processor 130, 230 or 330, the first display setting 150, 250 or 350 based on the first analysis result 112, 212 or 312; and step S830 of executing, by the at least one processor 130, 230 or 330, the first display setting 150, 250 or 350 so that the first medical image 140, 240 or 340 and the first analysis result 112, 212 or 312 are displayed on the screen based on the first display setting 150, 250 or 350.

In step S830 of executing the first display setting 150, 250 or 350, the at least one processor 130, 230 or 330 may execute the first display setting 150, 250 or 350 to include the user menu configured to receive whether a user approves the first analysis result 112, 212 or 312 displayed on the screen based on the first display setting 150, 250 or 350.

In step S820 of generating the first display setting 150, 250 or 350, the at least one processor 130, 230 or 330 may generate the first display setting 150, 250 or 350 based on at least one of the type of disease, the type of lesion, and a quantitative measurement result of the lesion detected in the first medical image 140, 240 or 340 and indicated by the first analysis result 112, 212 or 312.

The first display setting 150, 250 or 350 may include settings for at least one view of the first medical image 140, 240 or 340 related to the first analysis result 112, 212 or 312, a menu adapted to display the first analysis result 112, 212 or 312 in the first medical image 140, 240 or 340, the layout of the at least one view of the first medical image 140, 240 or 340, and a user menu adapted to allow a user to respond to the first analysis result 112, 212 or 312 displayed in the first medical image 140, 240 or 340.

In step S820 of generating the first display setting 150, 250 or 350, when the types of diseases detected in the first medical image 140, 240 or 340 and included in the first analysis result 112, 212 or 312 are plural in number, the at least one processor 130, 230 or 330 may generate a plurality of sub-display settings for a plurality of types of diseases, respectively.

In step S830 of executing the first display setting 150, 250 or 350, the at least one processor 130, 230 or 330 may arrange the plurality of sub-display settings in separate areas on the screen, and may display a first sub-display setting among the plurality of sub-display settings on the screen. In this case, when the first sub-display setting is preferentially displayed on the screen, the at least one processor 130, 230 or 330 may display another sub-display setting instead of the first sub-display setting on the screen in response to user input.

The first artificial neural network 110, 210 or 310 may be an artificial neural network including the function of diagnosing a plurality of types of diseases for a single body part in a medical image.

Referring to FIGS. 2 and 8 together, the computing system 200 may include a second artificial neural network that is an artificial neural network that inputs a plurality of second display settings selected by an expert for a plurality of types of diseases diagnosed for a plurality of third medical images and learns the function of generating display settings based on the types of disease diagnosed. In this case, in step S820 of generating the first display setting 250 based on the first analysis result 212, the at least one processor 230 may input the first analysis result 212 to the second artificial neural network, and may control the second artificial neural network so that the first display setting 250 can be acquired through the inference of the second artificial neural network.

Referring to another embodiment of the present invention and FIG. 8, the computing system may further include a third artificial neural network that is an artificial neural network that receives a plurality of third display settings selected by an expert for a plurality of third analysis results obtained through the inference of the first artificial neural network for a plurality of third medical images and learns correlations between at least one of the type of disease, the type of lesion, and a quantitative measurement result of the lesion, detected in the plurality of third medical images and included in the plurality of third analysis results, and the plurality of third display settings. In this case, in step S820 of generating the first display setting based on the first analysis result, the at least one processor may input the first analysis result to the third artificial neural network, and may control the third artificial neural network so that the first display setting is acquired through the inference of the third artificial neural network.

The method according to an embodiment of the present invention may be implemented in the form of program instructions, and may be then recorded in a computer-readable storage medium. The computer-readable storage medium may include program instructions, data files, and data structures solely or in combination. Program instructions recorded on the storage medium may have been specially designed and configured for the present invention, or may be known to or available to those who have ordinary knowledge in the field of computer software. Examples of the computer-readable storage medium include all types of hardware devices specially configured to record and execute program instructions, such as magnetic media, such as a hard disk, a floppy disk, and magnetic tape, optical media, such as compact disk (CD)-read only memory (ROM) and a digital versatile disk (DVD), magneto-optical media, such as a floptical disk, ROM, random access memory (RAM), and flash memory. Examples of the program instructions include machine code, such as code created by a compiler, and high-level language code executable by a computer using an interpreter. These hardware devices may be configured to operate as one or more software modules in order to perform the operation of the present invention, and the vice versa.

According to the present invention, when it is desired to identify various types of lesions on a series of medical images in a workflow for a clinician or radiologist, a display layout designed to fit the diagnosis of each of the lesions may be implemented.

If a clinician or radiologist can devote time only to tasks that are directly related to reading, it will shorten reading time and increase the efficiency of a workflow.

According to the present invention, display layout settings appropriate for each type of lesion and disease based on image information and diagnostic information included in a medical image may be proposed by considering a plurality of types of lesions that can be detected in the same body part. Furthermore, according to the present invention, hanging protocols that execute the display layout settings may be provided based on information related to the type of lesion and disease detected in the medical image.

According to the present invention, there may be provided hanging protocols based on disease codes detected for medical images.

According to the present invention, execute hanging protocols based on disease codes detected in medical images in an environment having a CAD capable of detecting a plurality of types of lesions and reading time is shortened and the efficiency of a workflow is increased such that a clinician or radiologist can devote time only to tasks that are directly related to reading.

According to the present invention, there may be provided a user interface and display environment that increase the efficiency of reading, assists a clinician or radiologist in deriving a more accurate diagnosis result within a short period of time, and increase the accuracy of analysis.

However, the present invention is not limited to the embodiments. Like reference symbols in the drawings designate like components. The lengths, heights, sizes, widths, etc. introduced in the embodiments and drawings of the present invention may be exaggerated to help to understand.

Although the present invention has been described with reference to specific details such as the specific components, and the limited embodiments and drawings, these are provided merely to help a general understanding of the present invention, and the present invention is not limited thereto. Furthermore, those having ordinary skill in the technical field to which the present invention pertains may make various modifications and variations from the above detailed description.

Therefore, the spirit of the present invention should not be defined based only on the described embodiments, and not only the attached claims but also all equivalent to the claims should be construed as falling within the scope of the spirit of the present invention.

What is claimed is:

1. A medical image reading assistant apparatus providing hanging protocols based on a medical artificial neural network, the medical image reading assistant apparatus comprising a computing system, the computing system comprising at least one processor, wherein the at least one processor is configured to:
    acquire or receive a first analysis result obtained through an inference of a first artificial neural network from a first medical image;
    generate a first display setting based on the first analysis result; and
    execute the first display setting by controlling a display device so that the first medical image and the first analysis result are displayed on a screen of the display device based on the first display setting,
    wherein the first display setting includes a layout of a plurality of visual expressions of the first medical image.

2. The medical image reading assistant apparatus of claim 1, wherein the at least one processor is further configured to execute the first display setting to include a user menu adapted to receive information about whether a user approves the first analysis result displayed on the screen based on the first display setting.

3. The medical image reading assistant apparatus of claim 1, wherein the at least one processor is further configured to generate the first display setting based on at least one of a type of disease, a type of lesion, or a quantitative measurement result of the lesion detected in the first medical image and indicated by the first analysis result.

4. The medical image reading assistant apparatus of claim 1, wherein the first display setting comprises settings for at least one view of the first medical image related to the first analysis result, a menu adapted to display the first analysis result in the first medical image, a layout of the at least one view of the first medical image, and a user menu adapted to allow a user to respond to the first analysis result displayed in the first medical image.

5. The medical image reading assistant apparatus of claim 1, wherein the at least one processor is further configured to:
    when types of diseases detected in the first medical image and included in the first analysis result are plural in number, generate a plurality of sub-display settings for the plurality of types of diseases, respectively; and
    arrange the plurality of sub-display settings in separate areas on the screen, or preferentially display a first sub-display setting among a plurality of sub-display settings on the screen and display another sub-display setting instead of the first sub-display setting on the screen in response to user input.

6. The medical image reading assistant apparatus of claim 1, wherein the first artificial neural network is an artificial neural network including a function of diagnosing a plurality of types of diseases for a single body part in a medical image.

7. The medical image reading assistant apparatus of claim 6, wherein the first artificial neural network is implemented by combining a plurality of sub-artificial neural network modules including a function of diagnosing a single type of disease for a single body part in a medical image.

8. The medical image reading assistant apparatus of claim 6, wherein the first artificial neural network is an artificial neural network that has learned a function of diagnosing a plurality of types of diseases for a single body part included in a plurality of second medical images by receiving information obtained by at least an expert diagnosing a plurality of types of diseases for the single body part included in the plurality of second medical images.

9. The medical image reading assistant apparatus of claim 1, wherein:
    the computing system further comprises a third artificial neural network that is an artificial neural network that receives a plurality of third display settings selected by at least an expert for a plurality of third analysis results obtained through an inference of the first artificial neural network for a plurality of third medical images and learns correlations between at least one of a type of disease, a type of lesion, and a quantitative measurement result of the lesion, detected in the plurality of third medical images and included in the plurality of third analysis results, and the plurality of third display settings; and
    the at least one processor is further configured to:
        input the first analysis result to the third artificial neural network; and
        control the third artificial neural network so that the first display setting is acquired through an inference of the third artificial neural network.

10. A medical image reading assistant apparatus providing hanging protocols based on a medical artificial neural network, the medical image reading assistant apparatus comprising a computing system, the computing system comprising at least one processor, wherein the at least one processor is configured to:
    acquire or receive a first analysis result obtained through an inference of a first artificial neural network from a first medical image;
    generate a first display setting based on the first analysis result; and
    execute the first display setting by controlling a display device so that the first medical image and the first analysis result are displayed on a screen of the display device based on the first display setting, wherein:

the computing system further comprises a second artificial neural network that is an artificial neural network that has learned a function of generating display settings based on the types of diagnosed diseases by receiving a plurality of second display settings selected by at least an expert for a plurality of types of diseases diagnosed for a plurality of third medical images; and the at least one processor is further configured to:

input the first analysis result to the second artificial neural network; and control the second artificial neural network so that the first display setting is acquired through an inference of the second artificial neural network.

11. An artificial neural network-based medical image reading assistant method, the artificial neural network-based medical image reading assistant method being performed by program instructions executed by a computing system, the computing system comprising at least one processor, the artificial neural network-based medical image reading assistant method comprising:

acquiring or receiving, by the at least one processor, a first analysis result obtained through an inference of a first artificial neural network from a first medical image;

generating, by the at least one processor, a first display setting based on the first analysis result; and executing, by the at least one processor, the first display setting by controlling a display device so that the first medical image and the first analysis result are displayed on a screen of the display device based on the first display setting, wherein the first display setting includes a layout of a plurality of visual expressions of the first medical image.

12. The artificial neural network-based medical image reading assistant method of claim 11, wherein the executing the first display setting comprises executing, by the at least one processor, the first display setting to include a user menu adapted to receive information about whether a user approves the first analysis result displayed on the screen based on the first display setting.

13. The artificial neural network-based medical image reading assistant method of claim 11, wherein the executing the first display setting comprises generating, by the at least one processor, the first display setting based on at least one of a type of disease, a type of lesion, or a quantitative measurement result of the lesion detected in the first medical image and indicated by the first analysis result.

14. The artificial neural network-based medical image reading assistant method of claim 11, wherein the first display setting comprises settings for at least one view of the first medical image related to the first analysis result, a menu adapted to display the first analysis result in the first medical image, a layout of the at least one view of the first medical image, and a user menu adapted to allow a user to respond to the first analysis result displayed in the first medical image.

15. The artificial neural network-based medical image reading assistant method of claim 11, wherein:

the executing the first display setting comprises, when types of diseases detected in the first medical image and included in the first analysis result are plural in number, generating a plurality of sub-display settings for the plurality of types of diseases, respectively; and the executing the first display setting comprises arranging the plurality of sub-display settings in separate areas on the screen, or preferentially displaying a first sub-display setting among a plurality of sub-display settings on the screen and displaying another sub-display setting instead of the first sub-display setting on the screen in response to user input.

16. The artificial neural network-based medical image reading assistant method of claim 11, wherein the first artificial neural network is an artificial neural network including a function of diagnosing a plurality of types of diseases for a single body part in a medical image.

17. The artificial neural network-based medical image reading assistant method of claim 11, wherein:

the computing system further comprises a third artificial neural network that is an artificial neural network that receives a plurality of third display settings selected by at least an expert for a plurality of third analysis results obtained through an inference of the first artificial neural network for a plurality of third medical images and learns correlations between at least one of a type of disease, a type of lesion, and a quantitative measurement result of the lesion, detected in the plurality of third medical images and included in the plurality of third analysis results, and the plurality of third display settings; and the generating a first display setting comprises inputting, by the at least one processor, the first analysis result to the third artificial neural network and controlling, by the at least one processor, the third artificial neural network so that the first display setting is acquired through an inference of the third artificial neural network.

18. An artificial neural network-based medical image reading assistant method, the artificial neural network-based medical image reading assistant method being performed by program instructions executed by a computing system, the computing system comprising at least one processor, the artificial neural network-based medical image reading assistant method comprising:

acquiring or receiving, by the at least one processor, a first analysis result obtained through an inference of a first artificial neural network from a first medical image;

generating, by the at least one processor, a first display setting based on the first analysis result; and executing, by the at least one processor, the first display setting by controlling a display device so that the first medical image and the first analysis result are displayed on a screen of the display device based on the first display setting, wherein:

the computing system further comprises a second artificial neural network that is an artificial neural network that has learned a function of generating display settings based on the types of diagnosed diseases by receiving a plurality of second display settings selected by at least an expert for a plurality of types of diseases diagnosed for a plurality of third medical images; and the generating a first display setting comprises inputting, by the at least one processor, the first analysis result to the second artificial neural network and controlling, by the at least one processor, the second artificial neural network so that the first display setting is acquired through an inference of the second artificial neural network.

* * * * *